US010325176B2

(12) United States Patent
Yin et al.

(10) Patent No.: US 10,325,176 B2
(45) Date of Patent: Jun. 18, 2019

(54) METHODS AND SYSTEMS FOR ASSESSING RETINAL IMAGES, AND OBTAINING INFORMATION FROM RETINAL IMAGES

(71) Applicant: AGENCY FOR SCIENCE, TECHNOLOGY AND RESEARCH, Singapore (SG)

(72) Inventors: Fengshou Yin, Singapore (SG); Wing Kee Damon Wong, Singapore (SG); Jiang Liu, Singapore (SG); Beng Hai Lee, Singapore (SG); Zhuo Zhang, Singapore (SG); Kavitha Gopalakrishnan, Singapore (SG); Ying Quan, Singapore (SG); Ai Ping Yow, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 107 days.

(21) Appl. No.: 15/506,708

(22) PCT Filed: Aug. 25, 2015

(86) PCT No.: PCT/SG2015/050275
§ 371 (c)(1),
(2) Date: Feb. 24, 2017

(87) PCT Pub. No.: WO2016/032397
PCT Pub. Date: Mar. 3, 2016

(65) Prior Publication Data
US 2018/0181833 A1     Jun. 28, 2018

(30) Foreign Application Priority Data

Aug. 25, 2014  (SG) ............................ 10201405206X

(51) Int. Cl.
*G06K 9/62* (2006.01)
*A61B 3/00* (2006.01)
(Continued)

(52) U.S. Cl.
CPC .......... *G06K 9/4676* (2013.01); *A61B 3/0025* (2013.01); *A61B 3/12* (2013.01);
(Continued)

(58) Field of Classification Search
None
See application file for complete search history.

(56) References Cited

U.S. PATENT DOCUMENTS 8,879,813 B1    11/2014  Solanki et al.
9,390,327 B2 *   7/2016  Gottemukkula ..... G06K 9/0061
(Continued)

FOREIGN PATENT DOCUMENTS

WO   WO 2003/030073 A1    4/2003
WO   WO 2013/184070 A1   12/2013
(Continued)

OTHER PUBLICATIONS

PCT International Search Report for PCT Counterpart Application No. PCT/SG2015/050275, 4 pp., (dated Sep. 24, 2015).
(Continued)

*Primary Examiner* — Nancy Bitar
(74) *Attorney, Agent, or Firm* — Womble Bond Dickinson (US) LLP

(57) ABSTRACT

A method of assessing the quality of an retinal image (such as a fundus image) includes selecting at least one region of interest within a retinal image corresponding to a particular structure of the eye (e.g. the optic disc or the macula), and a quality score is calculated in respect of the, or each, region-of-interest. Each region of interest is typically one associated with pathology, as the optic disc and the macula (Continued)

are. Optionally, a quality score may be calculated also in respect of the eye as a whole (i.e. over the entire image, if the entire image corresponds to the retina).

14 Claims, 11 Drawing Sheets

(51) Int. Cl.

| | | |
|---|---|---|
| G06K 9/46 | (2006.01) | |
| G06T 7/00 | (2017.01) | |
| G06K 9/03 | (2006.01) | |
| A61B 3/12 | (2006.01) | |
| A61B 3/14 | (2006.01) | |
| G06K 9/00 | (2006.01) | |

(52) U.S. Cl.
CPC .............. *A61B 3/14* (2013.01); *G06K 9/0061* (2013.01); *G06K 9/036* (2013.01); *G06K 9/6269* (2013.01); *G06T 7/0012* (2013.01); *G06T 7/0014* (2013.01); *A61B 2576/02* (2013.01); *G06K 2009/00932* (2013.01); *G06K 2209/05* (2013.01); *G06T 2207/20081* (2013.01); *G06T 2207/30041* (2013.01); *G06T 2207/30168* (2013.01)

(56) References Cited

U.S. PATENT DOCUMENTS

| | | | | |
|---|---|---|---|---|
| 9,819,864 | B2* | 11/2017 | Henriksen | A61B 3/12 |
| 2012/0150029 | A1* | 6/2012 | Debuc | A61B 3/102 |
| | | | | 600/425 |
| 2013/0222767 | A1 | 8/2013 | Cheng et al. | |
| 2015/0110372 | A1* | 4/2015 | Solanki | G06T 7/0014 |
| | | | | 382/130 |
| 2015/0265144 | A1* | 9/2015 | Burlina | A61B 3/10 |
| | | | | 351/206 |
| 2018/0315193 | A1* | 11/2018 | Paschalakis | G06T 7/0016 |

FOREIGN PATENT DOCUMENTS

| | | |
|---|---|---|
| WO | WO 2014/031086 A1 | 2/2014 |
| WO | WO 2014/074178 A1 | 5/2014 |

OTHER PUBLICATIONS

PCT Written Opinion of the International Searching Authority for PCT Counterpart Application No. PCT/SG2015/050275, 5 pp., (dated Sep. 24, 2015).

M. Niemeijer, et al., "Image structure clustering for image quality verification of color retina images in diabetic retinopathy screening," Medical image analysis, vol. 10, No. 6, pp. 888-898 (Dec. 2006).

Supplementary European Search Report for EP Application No. 15 83 6083, 4 pgs, (dated Feb. 23, 2018).

Honggang Yu, et al., "Automated image quality evaluation of retinal fundus photographs in diabetic retinopathy screening," XP032184067, 2012 IEEE Southwest Symposium on Image Analysis and Interpretation (SSIAI), pp. 125-128 (Apr. 22, 2012).

Ramon Pires, et al., "Retinal Image Quality Analysis for Automatic Diabetic Retinopathy Detection," XP032283151, 2012 25$^{th}$ SIBGRAPI Conference on Graphics, Patterns and Images, pp. 229-236 (Aug. 22, 2012).

Alan D. Fleming, et al., "Automated Assessment of Diabetic Retinal Image Quality Based on Clarity and Field Definition," XP055453632, Investigative Opthalmology & Visual Science, vol. 47, No. 3, pp. 1120-1125 (Mar. 1, 2006).

Andrew Hunter, et al., "An automated retinal image quality in grading algorithm," XP03232041, 33$^{rd}$ Annual International Conference of the IEEE EMBS, pp. 5955-5958 (Aug. 30, 2011).

PCT International Preliminary Report on Patentability for PCT Application No. PCT/SG2015/050275, 6 pgs, (dated Feb. 28, 2017).

\* cited by examiner (a)

(b)

(a)

(b)

(c)

(a)

(b)

(c)

(a)

(b)

METHODS AND SYSTEMS FOR ASSESSING RETINAL IMAGES, AND OBTAINING INFORMATION FROM RETINAL IMAGES

CROSS-REFERENCE TO RELATED APPLICATIONS

This patent application is a U.S. National Phase Application under 35 U.S.C. § 371 of International Application No. PCT/SG2015/050275, filed Aug. 25, 2015, entitled METHODS AND SYSTEMS FOR ASSESSING RETINAL IMAGES, AND OBTAINING INFORMATION FROM RETINAL IMAGES, which claims priority to Singapore Patent Application No. 10201405206X, filed Aug. 25, 2014.

FIELD OF THE INVENTION

The present invention relates to computer-implemented methods and apparatus for assessing images which are believed to be images of the retina of an eye, and, in the case that the images are determined to be of sufficient quality, for obtaining information from them, for suggesting a treatment.

BACKGROUND OF THE INVENTION

The major causes of blindness include cataracts, glaucoma, age-related macular degeneration, diabetic retinopathy, as well as pathological myopia. Of these, vision lost in cataracts can usually be restored by replacing the opacified crystalline lens with an artificial intra-operative lens. However, in many of the other diseases such as glaucoma and AMD, vision loss tends to be permanent and irrecoverable. Hence, there is considerable public and clinical interest to detect such diseases in as early a stage as possible, in order to save sight and reduce the costs of treatment. Early detection is often further complicated by the asymptomatic nature of many eye diseases, in which visual symptoms are usually only observed by the patient at an advanced stage of progression.

The retina is a layer of tissue which lines the inner surface of the eye. It is the light-sensitive part of the eye, on which the lens focuses light, which are then transmitted to the brain as signals for interpretation. Damage and degeneration of the retinal layer are key causes of permanent visual loss. In particular, there are two key areas within the retina known as the optic disk and the macula which have principal roles in the human visual system. These areas are marked on FIG. 1, which is a fundus image of the rear of an eye.

1. The Optic Disk

The optic disk is also known as the optic nerve head, and is the location in the retina where the ganglion nerve fibre cells aggregate to form the optic nerve, which connects the eye to the brain. It is through the optic nerve that signals are transmitted from the photoreceptors to the brain. The main disease associated with the optic disk is known as glaucoma.

Glaucoma is the leading cause of permanent blindness worldwide. In glaucoma, the degeneration of the ganglion nerve fibres results in vision loss. FIG. 2(a) shows schematically the vision loss associated with late stages of the disease. Early stages of glaucoma are usually not noticed by the subject. However, direct observation of the optic disk using modalities such as retinal imaging can be instructive in glaucoma detection. The degeneration of the retinal nerve fibres manifests as an enlargement of an excavation in the optic disk, which is known as the optic cup. An increased diameter of the optic cup in relation to the optic disk has been linked to glaucoma. This is illustrated in FIG. 3, where FIG. 3(a) shows the optic disc of a normal eye, and FIG. 3(b) shows the optic disc having an elevated cup-disk-ratio (CDR).

In addition to glaucoma, pathological myopia can also be detected from observation of the optic disk. In pathological myopia, degenerative changes associated with axial elongation of the eyeball results in the appearance of peripapillary atrophy (PPA) around the optic disk. This is illustrated in FIG. 3(c).

2. The Macula

The macula is the central part of the retina that is responsible for detailed central vision and related tasks such as reading, driving or recognizing people. It is a highly pigmented region, located centrally in the retina and is temporal to the optic disk. The macula contains the highest concentration of photoreceptors in the eye. The disease most associated with the macula is known as Age Related Macular Degeneration (AMD). This produces the vision loss shown schematically in FIG. 2(b).

In AMD, degeneration of the macular region of the retina leads to a direct loss of vision in the center of the visual field. AMD primarily affects aging individuals, with prevalence increasing with age. The disease is usually broadly categorized into early and late stages, with a noticeable central scotoma appearing the later stages. The early stage of AMD is usually linked to the appearance of drusen and retinal pigment epithelium changes in the macula region. Such lesions can be observed from images of the retina. This is illustrated by FIG. 4, which shows images of (a) a normal macula, (b) a macula with drusen, and (c) a macula with a macula hole.

Other eye diseases which include macula-location specific lesions include diabetic retionopathy from the appearance of macula edemas, as well as pathological degeneration from the presence of macular holes and lacquer cracks.

The critical need to detect blinding eye diseases early and effectively in large populations has spurred the development of computer-aided tools in recent years. In particular, automatic computer-aided diagnosis and analysis techniques, from the detection of individual lesions and cues, to the detection of diseases at the image level, has seen rapid developments due to interest from policy makers, academics, clinicians and industry. Potentially, successful implementation of these technologies will lead to better, more effective and more efficient screening of such blinding diseases with large social and economic impact.

Many of these methods are developed based on datasets of clean, filtered images. Due to the necessity of assessing the performance of the algorithms and techniques on disease and lesion detection, clean, sharp and clear images are often selected for technique development, training and testing. This is often seen in many public databases for research and development, such as the DRIVE database, where images are of high quality.

However, in practice, such clean high-quality images are often difficult to acquire. This can be due to imaging artefacts from the misalignment of the acquisition optics, unexpected subject movement, or defocusing during image capturing. Other reasons could include the presence of cataracts in the subject, which act as opacities in the optical light path resulting in blurred images. FIGS. 5(a) and 5(b) are examples of poor-quality fundus images. When such images are encountered by the automated analysis systems, the results generated may not be reliable. This is because these systems are developed with the assumption that the images are of good quality, and any deviations from the norm are due to existing pathologies rather than imaging artefacts. Thus, the diagnosis results of such poor images can be inaccurate.

As the poor quality images are obtained during the acquisition process as part of the imaging optics or disease pathologies rather than as a result of compression, it is difficult to restore these images to an improved state without artificial interpolations. Thus, there remains a need to detect such poor quality images at a pre-processing level for filtering out before use in any computer-aided detection method.

Image quality assessment is of interest to many fields. Such methods can be divided into full-reference and no-reference methods. Full-reference methods are ones in which the image to be assessed is compared to a reference image of the same image subject which is assumed to have perfect quality. Such methods are mainly used to compare the effects of image compression algorithms, and have little relevance to the present task. Instead, we focus on no-reference methods.

P1: Distribution-Based Method

This method uses histograms of the global distributions of the edges and local image histograms. The histograms are modelled as Rayleigh distributions. A similarity measure is then used to determine the quality of the image against reference statistics. This is described at Lalonde, M., Gagnon, L. & Boucher, M. C. (2001). Automatic visual quality assessment in optical fundus images, Proceedings of Vision Interface, pp. 259-264.

P2: Segmentation-Based Method

In this method preliminary segmentation of the optic disk, vessels and macula are first performed using Hough transforms. Image quality is then determined using the visibility of fine vessels. This is combined with field information from the spatial locations of the optic disk and macula to generate a final score for the image. This is described at Fleming, A. D., Philip, S., Goatman, K. A., Olson, J. A. & Sharp, P. F. (2006). Automated assessment of diabetic retinal image quality based on clarity and field definition, Investigative Ophthalmology and Visual Science 47 (3): 1120-1125.

P3: Bag of Words-Based Method

This method uses two sets of features based on color using normalized histograms, and second order image structure invariants using multiscale Gaussian filters. Histograms of visual words were used to classify the image quality in a bag-of-words approach. This is described at Niemeijer, M., Abramoff, M. D. & van Ginneken, B. (2006). Image structure clustering for image quality verification of color retina images in diabetic retinopathy screening. Medical Image Analysis 10 (6): 888-898.

P4: Vessel and Color-Based Method

Color histograms are used together with vessel segmentation in the HSV color space as features in this method. The features are then combined in a Bag-of-Words technique similar to P3. In another method, a global score for noise and blur is first calculated based on anisotropic patches in an image. Then, a weighted quality score is obtained by incorporating variance of vessel information in local patches. This is described at: Giancardo, L., Abramoff, M. D., Chaum, E., Karnowski, T. P., Meriaudeau, F. & Tobin, K. W. (2008). Elliptical local vessel density: a fast and robust quality metric for retinal images, Proceedings of IEEE EMBS. See also Kohler, T., Budai, A., Kraus, M. F., Odstrcilik, J., Michelson, G., Hornegger, J., "Automatic no-reference quality assessment for retinal fundus images using vessel segmentation," Computer-Based Medical Systems (CBMS), 2013 IEEE 26th International Symposium on, vol., no., pp. 95, 100, 20-22 Jun. 2013.

SUMMARY OF THE INVENTION

The present invention aims to provide new and useful methods and systems for evaluating a retinal image. Optionally, any images which are determined to be of high quality are used to obtain information about an eye, which may be used—for example in combination with other information—to suggest a treatment for the eye.

In general terms, the present invention proposes that, as part of assessing the quality of a retinal image (such as a fundus image) at least one region of interest is selected within a retinal image corresponding to a particular structure of the eye (e.g. the optic disc or the macula), and a quality score is calculated in respect of the, or each, region-of-interest. Each region of interest is typically one associated with pathology, as the optic disc and the macula are.

Optionally, a quality score may be calculated also in respect of the eye as a whole (i.e. over the entire image, if the entire image corresponds to the retina).

This concept is in contrast to known image assessment methods which assess the quality of the entire image. Since imaging artefacts can be local, certain embodiments of the invention help to ensure that the usage of the input image is maximized by assessing the quality of the detected focal region of interest, rather than rejecting the entire image based on global characteristics.

If the initial region of interest is not suitable, another ROI may be extracted and re-assessed. This may be repeated until a suitable ROI is found, or when all possible ROI are exhausted. Thus, the invention makes it possible for useful results to be obtained in respect of a first ROI (e.g. the optic disc or macula), even though the quality of another ROI (e.g. the macular or optic disc) is poor, and/or even if the quality of the image as a whole is low. This is clearly of benefit in the case that acquiring a replacement image would be expensive.

Furthermore, if the embodiment is to be used in the computer aided diagnosis (CAD) of a medical condition which is associated with a specific region of interest, an embodiment of the invention can be used to obtain a reliable quality score for that region of interest, even if other areas of the image are of low quality. If that quality score indicates that the region of interest is of sufficient quality, the corresponding part of the image can be used as part of the CAD process, yielding a reliable result.

Preferably, the invention also includes a process of checking automatically that a input image is of the correct image type (e.g. a fundus image).

An embodiment of the invention can be easily used in current technologies without the need for extensive modifications. For example, an embodiment can be used in two scenarios.

1) It can be used as a pre-filter for current automated disease detection systems by assessing the quality of retinal interest regions. Further, by successively applying the embodiment onto subsequent regions, the image can be fully probed to find a useable region instead of rejecting the image based on global quality. The embodiment may ensure that input regions are of usable quality, and provide feedback on the reliability of results based on retinal interest quality.

2) An embodiment of the invention may also be used during acquisition, to aid the photographer in capturing a good retinal interest region or overall image. For example, by applying the embodiment to an image which the photographer has captured, it may be determined whether another retinal image needs to be captured.

Embodiments of the invention may be used to improve the reliability of existing retinal image processing systems, provide a way to control the input quality, as well as a potential acquisition tool, through considering useful retinal interest regions or the whole image.

The invention may be expressed as a computer-implemented method of assessing the quality of an image, or as a computer-implemented method for performing a CAD using an input image including a pre-step of checking that the quality of at least a part of the input image is of sufficient quality. The invention may also be expressed as a computer programmed to perform such a method, or as a computer program product (e.g. stored on a tangible recording medium in non-volatile storage) including program instructions to be run by the computer to perform such a method.

Optionally, following the CAD further tests may be done, for example in that case that a medical condition has been diagnosed using the present techniques a more sophisticated (expensive) method may be used to verify the diagnosis.

Eventually, depending on the diagnosis, a medical treatment may be suggested, and even performed.

BRIEF DESCRIPTION OF THE FIGURES

A non-limiting embodiment of the invention will now be described for the sake of example only, with reference to the following figures in which.

DETAILED DESCRIPTION OF THE EMBODIMENT

Figure 1:
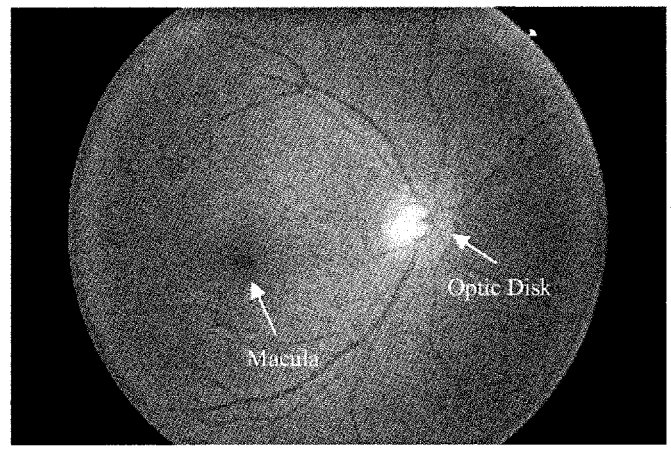
FIG. 1 is a typical fundus image of the eye with the optic disc and macular marked.
Figure 2:
FIG. 2, which is composed of FIGS. 2(a) and 2(b), shows schematically the vision loss associated with (a) glaucoma and (b) age-related macular degeneration.
Figure 2:
Figure 3:
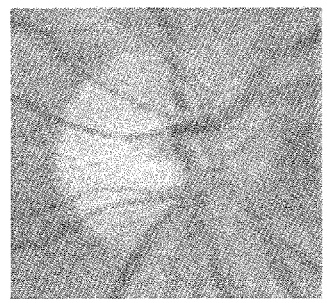
FIG. 3, which is composed of FIGS. 3(a)-(c) shows the portion of a fundus image representing the optic disk, in the case of (a) a normal eye, (b) an optic disc with a high cup-disk-ration, and (c) an optic disc with PPA.
Figure 3:
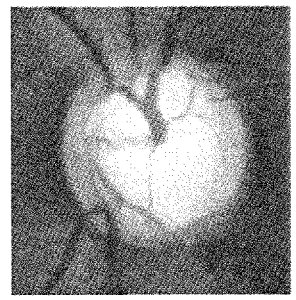
Figure 3:
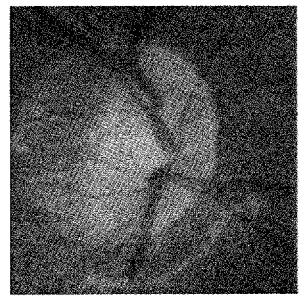
Figure 4:
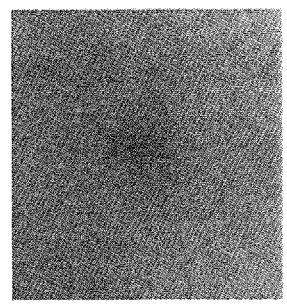
FIG. 4, which is composed of FIGS. 4(a)-(c) shows the portion of a fundus image representing the macula, in the case of (a) a normal macula, (b) a macula with drusen, and (c) a macula with a macula hole.
Figure 4:
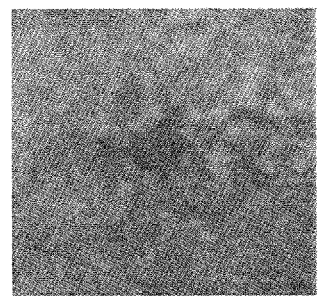
Figure 4:
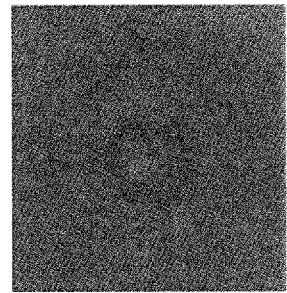
Figure 5:
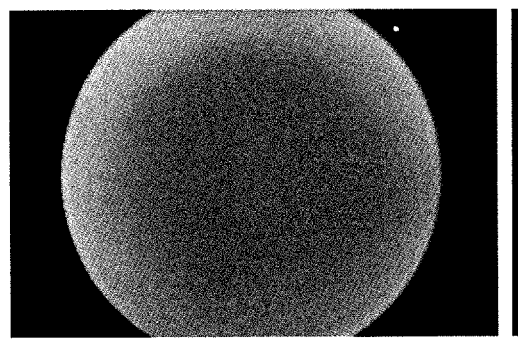
FIG. 5 is composed of FIGS. 5(a) and 5(b) which are typical poor quality images.
Figure 5:
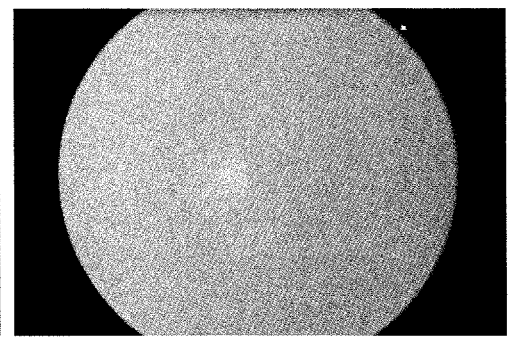
Figure 6:
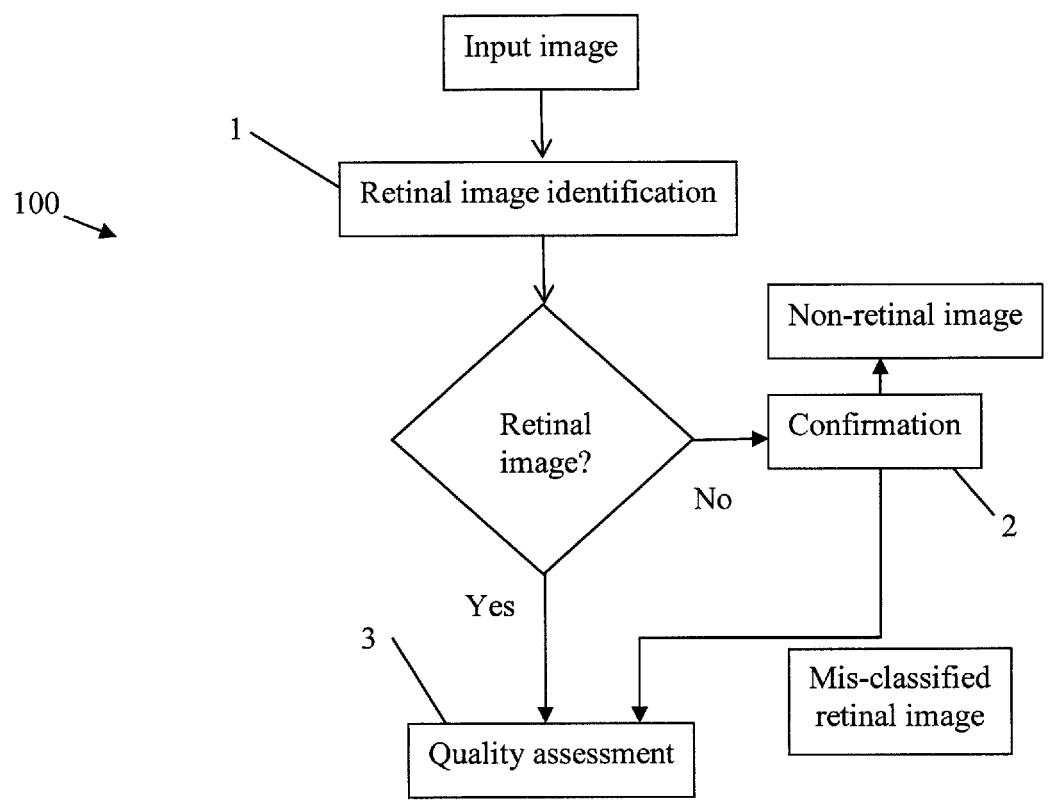
FIG. 6 is a flowchart of a method which is an embodiment of the invention.

Referring firstly to FIG. 6, a flow diagram is shown of a method 100 which is an embodiment of the method. The embodiment is referred to as ARIES (an Automated Retinal Interest Estimator System). ARIES automatically assesses the quality of input images as a pre-processing step before passing the processed images for subsequent analysis. In this way, ARIES will control the quality of input for subsequent analysis.

A key feature of ARIES is that it analyzes at least one of the focal regions of interest. A specific example here is the optic disk. Since imaging artefacts can be local, ARIES will help to ensure that the usage of the input image is maximized by assessing the quality of the detected focal region of interest, rather than rejecting the entire image based on global characteristics. If the initial region of interest is not suitable, another ROI will be extracted and re-assessed. This is repeated until a suitable ROI is found, or when all possible ROI are exhausted. ARIES assesses the quality of an input image in three steps: a retinal image identification step 1 in which an initial assessment is made of whether an input image is a retinal image; if the initial assessment is negative, a step 2 of re-evaluation of the image for confirmation 2; if the initial assessment was positive, or if the confirmation step 2 indicates the image was after all a retinal image (i.e. the initial assessment step 1 reached the wrong conclusion), a quality assessment step 3, to generate a full image quality score and a focal region (optic disc or macula) quality score will be given. These can be used to filter out low quality images or provide a warning of low confidence for further steps of processing.

1. Retinal Image Identification Step

The retinal and non-retinal image identification step 1 is important in filtering out irrelevant images in the computer aided diagnosis (CAD) of ocular diseases. A robust CAD system should be able to identify and isolate images of unknown types, and only process those with the correct image type.

Figure 7:
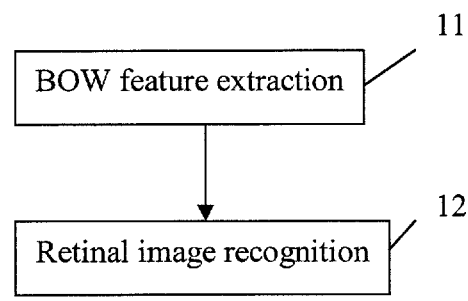
FIG. 7 shows the sub-steps of a retinal image identification step of the method of FIG. 6.

FIG. 7 shows the sub-steps of a possible implementation of step 1, which utilizes a weakly-supervised learning approach. In this approach, we can decide whether an image exhibits certain characteristics with no segmentation of objects or manual selection of features. In the first sub-step 11, the training images are represented using a bag of visual words representation, to generated a plurality of extracted features. In sub-step 12, the extracted features are used by a Support Vector Machine (SVM) classifier to generate a classification result.

The SVM was obtained by training using a training set comprising a plurality of each images, and for each image the extracted features obtained by the bag of visual words representation, and a respective label indicating whether the images was a retinal image. Once this is done, the trained SVM classifier can be applied to test on new images.

Figure 8:
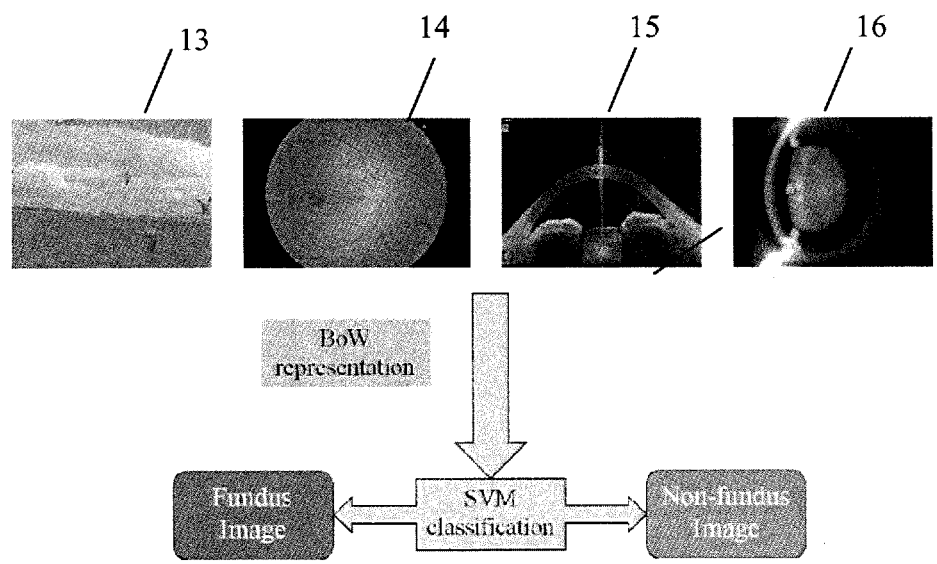
FIG. 8 is a schematic version of FIG. 7.

In one case, step 2 may be used to identify specifically whether the input image is a fundus image. In this case, the labels indicate whether each of the images in the training set is a fundus image or a non-fundus image. The latter classification is used even for input images which are another type of retinal image, such as Retcam images, OCT images and slit-lamp images. This process is shown schematically in FIG. 8. Although input images 14, 15 and 16 are all ocular images (input image 13 is not), only input image 14 is a fundus image, and is classified as such.

2. Confirmation Step

Artifacts in fundus images can affect the accuracy of the image classification in the previous step. Artefacts, especially overexposure, often lead to wrong classification of fundus images into non-fundus types. Thus, a confirmation step 2 is desirable to distinguish between real non-fundus images and fundus images with artefacts which led to misclassification in step 1. The identified fundus image with artefacts can be classified as poor quality fundus image directly or be fed to ARIES quality assessment step to assess focal regions.

Figure 9:
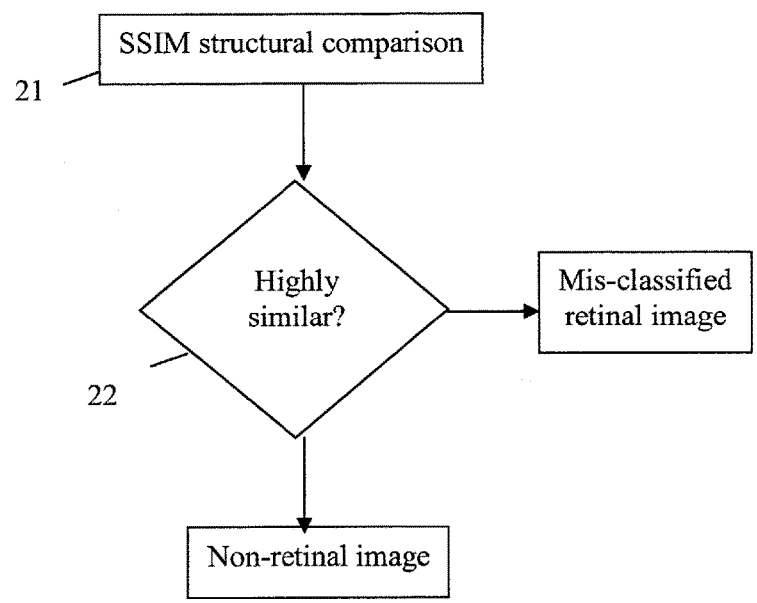
FIG. 9 shows the sub-steps of a confirmation step of the method of FIG. 6.

In order to reduce the misclassification rate, we introduce a confirmation method based on the structural similarity index (SSIM). The sub-steps of the confirmation step 2 are shown in FIG. 9. SSIM is a method for measuring the similarity between two images. Certain prior art techniques use a full reference metric designed to improve on traditional metrics such as PSNR and MSE by considering image degradation as perceived change in structural information. The SSIM between two windows x and y is:

$$SSIM(x, y) = \frac{(2u_x u_y + c_1)(2\sigma_{xy} + c_2)}{(u_x^2 + u_y^2 + c_1)(\sigma_x^2 + \sigma_y^2 + c_2)}$$

where $u_x$ and $u_y$ are the average, $\sigma_x^2$ and $\sigma_y^2$ are the variance, $\sigma_{xy}$ is the covariance of x and y respectively.

However, SSIM is used in a different way in step 2. Instead of the full reference approach, a reference image is generated by averaging a set of high quality fundus images. The input images are compared one-by-one to this reference image, to generate respective SSIM values (sub-step 21). The SSIM values may be compared with a predefined threshold value, thereby obtaining a decision of whether the images are fundus images or not (sub-step 22).

Figure 10:
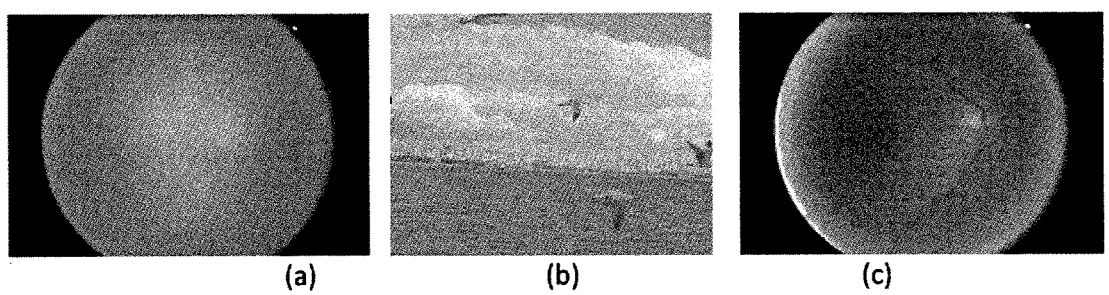
FIG. 10 is composed of FIG. 10(a), which is a reference retinal image, FIG. 10(b) which is not a fundus image, and FIG. 10(c) which is a fundus image with some artefacts.

Intuitively, non-fundus images such as scenery images and other ocular images should have low SSIMs. By contrast, fundus images with artefacts such as overexposed images should have high SSIMs. Therefore, we can separate overexposed fundus images from non-fundus images. FIG. 10 shows how this happens. FIG. 10(a) is the mean fundus image FIG. 10(b) show a non-fundus image (in fact, an image of scenery), having an SSIM of 0.42. FIG. 10(c) shows a poor quality fundus image, which nevertheless has an SSIM of 0.73. Thus, FIG. 10(c) is recognised as a fundus image if the threshold is below this value.

Note that in the process of FIG. 6, SSIM is used in the confirmation step, rather than in the initial retinal image identification step. This is because we have found that SSIM is of lower accuracy in image identification than the BoW process described, but it is accurate in identifying misclassified retinal images and non-retinal images. If the confirmation step is omitted, some very low quality fundus images may be misclassified as non-retinal images.

3. Image Quality Assessment of Retinal Images

Figure 11:
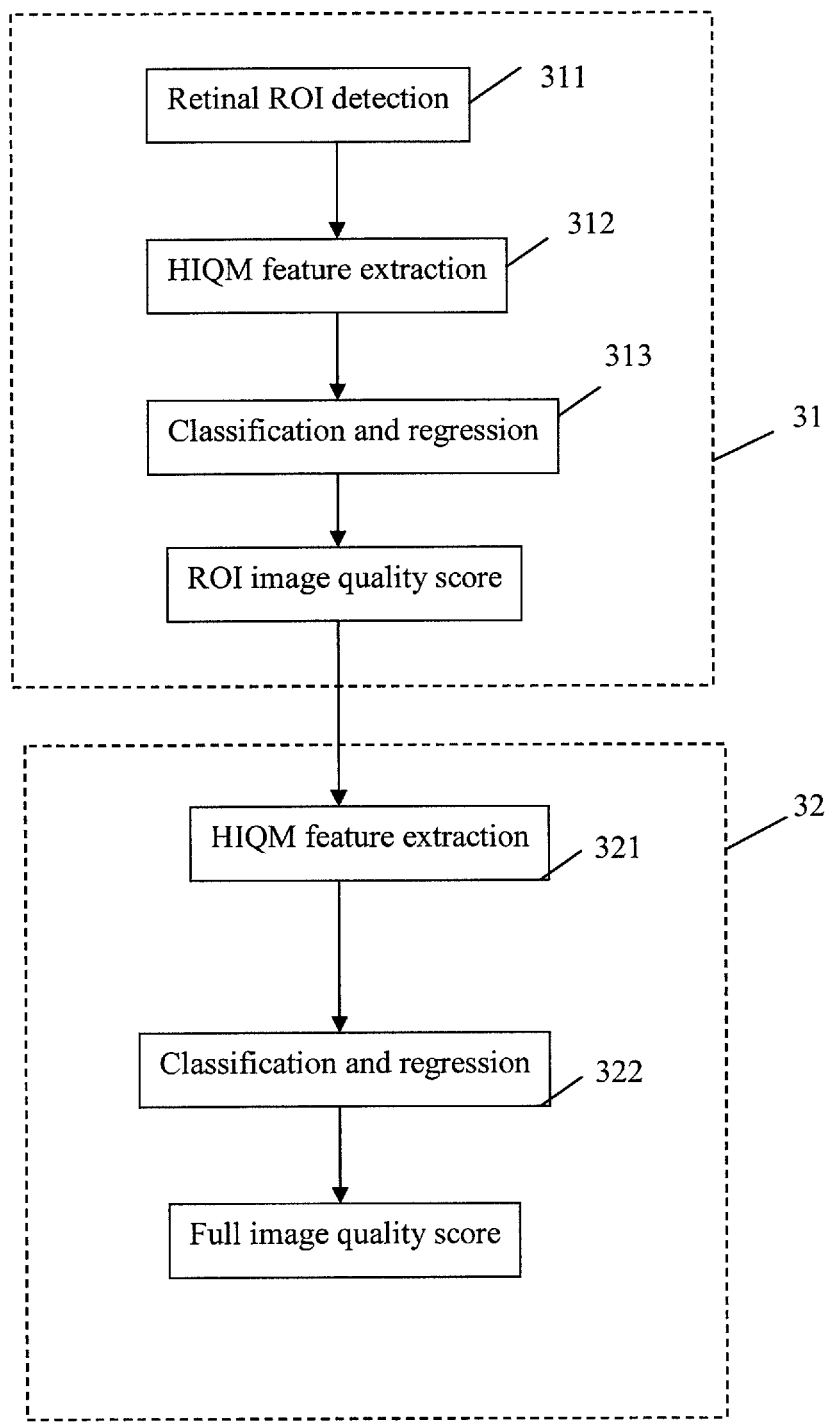
FIG. 11 shows the sub-steps of a quality assessment step of the method of FIG. 6.

The image quality assessment step 3 distinguishes retinal images with high quality from those with poor quality. As described previously, ARIES assesses focal regions of the image as well as the whole image. The process is illustrated in FIG. 11, and includes a sub-step of ROI quality assessment 31 and a sub-step 32 of full image quality assessment. Sub-step 32 may be performed more than once, each time using different structural regions of the eye to be the ROI (e.g. once with the ROI corresponding to the optic disc, and once with the ROI corresponding to the macula).

It is to be appreciated that sub-steps 31 and 32 are independent, and thus may be performed in the opposite order or even in parallel.

Thus, the first sub-sub-step of the focal region image quality assessment 31 is to detect a focal region of interest (ROI) 311. In fact, the embodiment tries to detect a plurality of ROIs in a pre-determined order. If the first ROI according to this pre-determined order cannot be detected, another ROI will be extracted and assessed. This is repeated for a pre-determined sequence of possible ROIs until a suitable ROI is found, or when all possible ROI are exhausted. In other words, when a certain ROI has been detected with high accuracy, the embodiment does not test the remaining ROIs on the predetermined list. The success rate of initial ROI detection for high quality images is very high. Thus, only images that fail the initial quality test will go through the process repeatedly.

Subsequently, high level image quality measures (HIQM) are extracted from the ROI image 312 to form the feature space. Finally, a SVM classification is performed 313, to generate a ROI image quality score. The full image quality assessment process 32 follows a similar flow except that the full image rather than ROI image is used to extract the HIQM features. Thus, sub-step 32 includes a sub-sub-step 321 of HIQM feature extraction, and a sub-step 322 of classification and regression, which can be performed by a SVM classification, giving a full image quality score.

The ROI image quality score(s) and full image quality score are general quality scores, and may be used in various ways according to the application. One option is to compare any one or more of them to respective thresholds, and then to reject them (at least for certain purposes) if the score(s) are below the threshold. For example, if the quality score for a first of the ROIs is below the threshold but the quality score for a second ROI is above the threshold, then the image may be rejected for use in obtaining information about the first ROI, but it may still be used to obtain information about the first ROI. However, this may be conditional on the full image quality score being above a respective threshold.

In the following text, we will illustrate the process using the optic disc image.

a) Sub-Sub-Step 311: Optic Disc ROI Detection

In optic disc (OD) localization, we first find a pixel that belongs to the OD. The region-of-interest (ROI) is a cropped sub-image from the original image that contains the OD. The OD is normally brighter than other regions of the fundus image. However, due to uneven illumination or an out-of-focus image, the fringe of the eyeball can also be very bright. In order to detect the OD centre accurately based on intensity values, we identified bright fringes and removed them. The fringe was extracted by locating a circle slightly smaller than the eyeball in the greyscale image and thresholded for high intensity pixels outside the circle. The fringe-removed image can be obtained by subtracting the bright fringe from the greyscale image. This image is then thresholded to obtain the top 0.5% of pixels in intensity. The centre of the OD is approximated by the centroid of the remaining bright pixels. The ROI is then defined as an image that is about twice the diameter of the normal OD.

Figure 12:
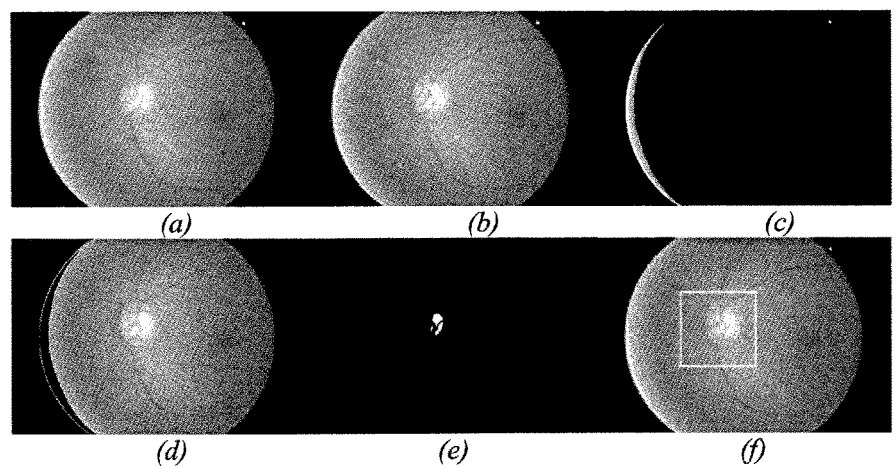
FIG. 12 which is composed of FIGS. 12(a)-(f), shows a process of detecting a ROI for an optic disc.

An example of the OD localization and ROI detection is shown in FIG. 12. FIG. 12(a) is the original image (shown as black-and-white, but in fact the original image is in colour; FIG. 12(b) is a greyscale image obtained from the original image; FIG. 12(c) shows the extracted high intensity fringe; FIG. 12(d) is the image of FIG. 12(b) with the high intensity fringe removed; FIG. 12(e) shows the thresholded high intensity pixels; and FIG. 12(f) shows by a white rectangle the portion of the image of FIG. 12(b) which is extracted as the ROI.

b) Sub-Sub-Step 312 HIQM Feature Extraction

Instead of using low level image features that have extremely high dimensions, we propose to use high level image quality measures (HIQM) for their high relevance to the problem the embodiment addresses, and their low dimensionality and hence fast speed. There are three categories of HIQM features and they are summarized as follows.

Contrast and Blur Features

High level contrast and blurriness measures include the contrast ratio measurements, the blur measures, the intensity ranges, and saturation metrics.

Contrast ratio is calculated as $$CR_j = \frac{\overline{p}_j}{s_j}$$

where $\overline{p}_j = mean(I_j)$ is the mean intensity of all the pixels in channel j of the image I in RGB color space, $s_j = std(I_j)$ is the standard deviation of all the pixel intensities, and j can be red channel r, green channel g, blue channel b and greyscale gs.

Higher contrast ratios correspond to higher blurriness. It is intuitively true as blur images usually have small variance in intensity, which leads to a high contrast ratio. Similar to contrast ratio, we also use the local contrast ratio on non-overlapping sub-windows of the image, which is defined as $$LCR = \frac{\sum_{i=1}^{n} \frac{\overline{p}_{w,i}}{s_{w,i}}}{n}$$

where w is an N×N pixel window, and n is the total number of sub-windows.

Blur metric (BM) is based on the discrimination between different levels of blur perceptible on the same picture. It requires no reference to compute and has a low cost implementation. This measure is robust in measuring focal blur and motion blur. Mathematically, it is obtained by comparing the intensity variations of the original image and its blurred version by a low-pass filter.

Intensity ranges, including full intensity range (R), relative intensity range and interquartile range (IQR), are important metrics to measure the greyscale spread of images. Image with high quality or contrast usually has a larger intensity range compared to one with low quality.

$$R = \max(I) - \min(I)$$
$$RR = \frac{\max(I) - \min(I)}{\operatorname{mean}(I)}$$
$$IQR = Q_3(I) - Q_1(I)$$

where I is the array of all pixel intensities of a greyscale image, $Q_1$ and $Q_3$ are the $1^{st}$ and $3^{rd}$ quartile values.

Saturation metrics include percentage of maximal (Pmax) and percentage of minimal (Pmin), measuring the proportions of pixels at the highest intensity and the lowest intensity respectively. The former is useful to identify over-exposed images; while the latter is able to identify under-exposed images.

Entropy Features

Entropy of an image can be used to represent the amount of information in it. It is calculated as:

$$E = -\sum_i p_i \log_2(p_i)$$

where $p_i$ is the probability that the difference between two adjacent pixels is equal to i.

If an image has been perfectly histogram equalized, the spread of greyscale values is at maximum. Thus, this image has maximum entropy. On the other hand, the entropy for a binary image is very low as it has only two states. If an image has flat-value pixels, the entropy is zero.

For optic disc region of interest, a high quality image should contain clear structure of optic disc, optic cup and blood vessels, which corresponds to high image entropy. On the other hand, a poor quality image does not contain fine features of those structures and thus has low image entropy.

Image Structure Features

The optic disc region has a high density of blood vessels. Thus, blood vessel density (BVD) can be used as an important feature to distinguish between low quality and high quality optic disc images.

Figure 13:
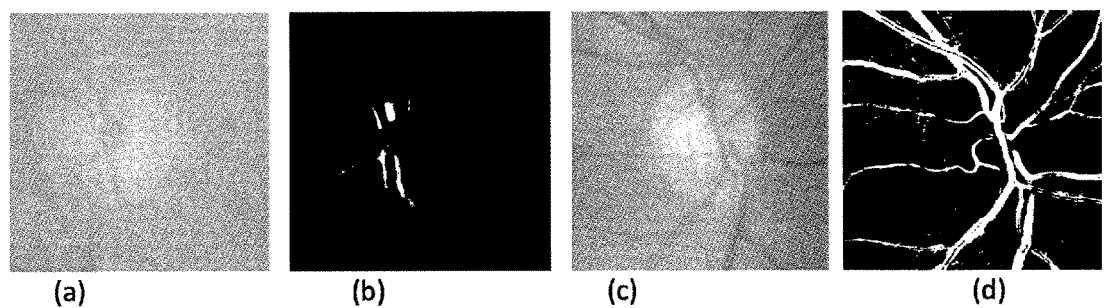
FIG. 13 is composed of FIGS. 13(a)-(d), which show optic disc ROIs from two different fundus images, and their respective vascular structures.

FIG. 13 illustrates the difference of detected vasculatures of two different images, shown as 13(a) (a low-quality image) and 13(c) (a high quality image). The corresponding detected blood vessels are shown in FIGS. 13(b) and 13(d).

Another important structure feature is the maximum edge length or edge spread (ES). The edges of blood vessels and optic disc boundary are usually continuous for a high quality image, as is the maximum edge spread. To compute BVD and ES, we first detect blood vessels in the image using a fast bottom-hat filtering method. The bottom-hat filter is applied to the histogram equalized green channel image (g) to obtain g̃. Subsequently, the blood vessel map M is determined by $$M(i, j) = \begin{cases} 1 & \tilde{g}(i, j) > T \\ 0 & \text{otherwise} \end{cases}$$

After obtaining the vessel map, BVD can be obtained through $$BVD = \frac{\sum_{i=1, j=1}^{m,n} M(i, j)}{m \times n}$$

where m and n represent the width and height of the image respectively.

The edge spread is calculated as the maximum major axis length of all connected components in M divided by the diagonal length of the image.

$$ES = \frac{\max(l_1, l_2, \ldots, l_k)}{\sqrt{m^2 + n^2}}$$

where l represents the major axis length of each connected component in M. Therefore, combining all three categories of features, HIQM contains 38 high level image quality measures. These features will be used in the next step.

c) Sub-Sub-Step 313 Image Quality Classification and Assessment

In the sub-sub-step 313, a support vector machine (SVM) is used to train the classifier. The SVM-based classification can be formulated as a quadratic programming problem with linear constraint:

$$\min_{w,b,\xi} \frac{1}{2} \omega^T \omega + C \sum_{i=1}^{N} \xi_i$$

subject to $y_i(\omega^T \phi(x_i) + b) \geq 1 - \xi_i$ $\xi_i \geq 0, i = 1, \ldots, N$ where $x_i$ is the training vector, $y_i$ is the training label, $\omega$ is the normal vector, b is the offset, $\xi_i$ is the slack variable to implement soft margin, C is the penalty term and $\phi$ is the kernel function.

Instead of using binary classification results only from SVM, the outputs of the SVM decision function (decision value) are also used. We normalized the decision values to produce an retinal image quality score (RQS):

$$RQS = wd + b$$

where d represents the decision value, w and b are constant coefficients. RQS have values from 0 to 1, with higher value represents better image quality.

Sub-sub-steps 321 and 322 are performed in the same way as sub-sub-steps 312 and 313 respectively to generate a ROI image quality score for the input image as a whole.

Figure 14:
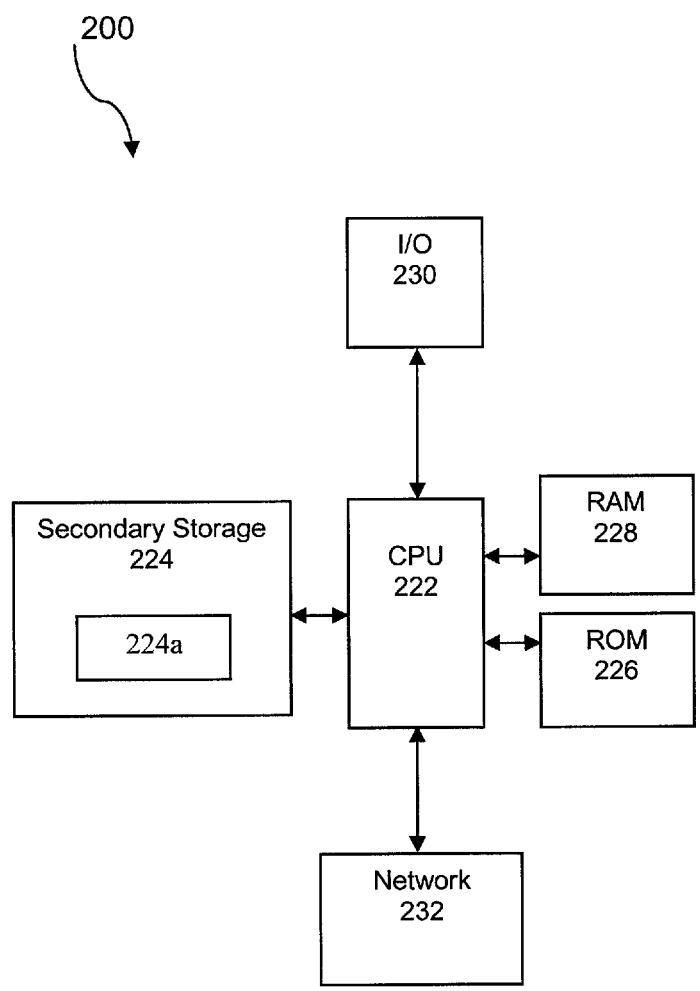
FIG. 14 shows the technical architecture of a computer system for performing the method.

FIG. 14 shows a technical architecture of computer system 200 which can be used to implement the embodiment of FIG. 6. The technical architecture includes a processor 222 (which may be referred to as a central processor unit or CPU) that is in communication with memory devices including secondary storage 224 (such as disk drives), read only memory (ROM) 226, random access memory (RAM) 228. The processor 222 may be implemented as one or more CPU chips. The technical architecture may further comprise input/output (I/O) devices 230, and network connectivity devices 232.

The secondary storage 224 is typically comprised of one or more disk drives or tape drives and is used for non-volatile storage of data and as an over-flow data storage device if RAM 228 is not large enough to hold all working data. Secondary storage 224 may be used to store programs which are loaded into RAM 228 when such programs are selected for execution.

In this embodiment, the secondary storage 224 has an order processing component 224a comprising non-transitory instructions operative by the processor 222 to perform various operations of the method of the present disclosure. The ROM 226 is used to store instructions and perhaps data which are read during program execution. The secondary storage 224, the RAM 228, and/or the ROM 226 may be referred to in some contexts as computer readable storage media and/or non-transitory computer readable media.

I/O devices 230 may include printers, video monitors, liquid crystal displays (LCDs), plasma displays, touch screen displays, keyboards, keypads, switches, dials, mice, track balls, voice recognizers, card readers, paper tape readers, or other well-known input devices.

The network connectivity devices 232 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), world-wide interoperability for microwave access (WiMAX), near field communications (NFC), radio frequency identity (RFID), and/or other air interface protocol radio transceiver cards, and other well-known network devices. These network connectivity devices 232 may enable the processor 222 to communicate with the Internet or one or more intranets. With such a network connection, it is contemplated that the processor 222 might receive information from the network, or might output information to the network in the course of performing the above-described method operations. Such information, which is often represented as a sequence of instructions to be executed using processor 222, may be received from and outputted to the network, for example, in the form of a computer data signal embodied in a carrier wave.

The processor 222 executes instructions, codes, computer programs, scripts which it accesses from hard disk, floppy disk, optical disk (these various disk based systems may all be considered secondary storage 224), flash drive, ROM 226, RAM 228, or the network connectivity devices 232. While only one processor 222 is shown, multiple processors may be present. Thus, while instructions may be discussed as executed by a processor, the instructions may be executed simultaneously, serially, or otherwise executed by one or multiple processors.

Although the technical architecture is described with reference to a computer, it should be appreciated that the technical architecture may be formed by two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the technical architecture 220 to provide the functionality of a number of servers that is not directly bound to the number of computers in the technical architecture 220. In an embodiment, the functionality disclosed above may be provided by executing the application and/or applications in a cloud computing environment. Cloud computing may comprise providing computing services via a network connection using dynamically scalable computing resources. A cloud computing environment may be established by an enterprise and/or may be hired on an as-needed basis from a third party provider.

It is understood that by programming and/or loading executable instructions onto the technical architecture, at least one of the CPU 222, the RAM 228, and the ROM 226 are changed, transforming the technical architecture in part into a specific purpose machine or apparatus having the novel functionality taught by the present disclosure. It is fundamental to the electrical engineering and software engineering arts that functionality that can be implemented by loading executable software into a computer can be converted to a hardware implementation by well-known design rules.

3. Experimental Results

The proposed system is studied on images from a range of fundus image databases such as the Singapore Malay Eye Study (SiMES), Singapore Chinese Eye Study (SCES) and Blue Mountains Eye Study (BMES). A number of non-fundus image databases such as slit-lamp images for, OCT images, Retcam images and scenery images are also used to test the retinal image identification. A summary of the databases used is shown in Table I. Images for subsequent quality assessments are from SiMES database. A detailed description is given below.

TABLE I

Database summary

| Database Name | Image Type | Number of Images |
|---|---|---|
| SiMES | Fundus | 5928 |
| SCES | Fundus | 1676 |
| BMES | Fundus | 6222 |
| Other Fundus | Fundus | 12314 |
| ACHIKO-NC | Slit-lamp | 5530 |
| AGAR Database | OCT | 1664 |
| AGATE Database | Retcam | 3699 |
| Scenery | Scenery | 4509 |
| Total | | 41542 |

The fundus image identification algorithm was trained on 6200 images, including 2700 fundus images and 3500 non-fundus images. It was tested on a batch of 35342 images, consisting of 23441 fundus images and 11902 non-funds images. The system achieves 99.54% accuracy in fundus and non-fundus image classification in the testing set.

In the training stage, 2700 fundus images, 500 OCT images, 500 Retcam images, 500 slit-lamp images and 2000 scenery images are randomly chosen as the training dataset. The rest of the images are used as the testing dataset. The summary of training of testing datasets and experiment results is shown in Table II.

TABLE II

Summary of experiment results for fundus image identification

| Database Name | Image Type | # Training Images | Accuracy on Training Set | # Testing Images | Accuracy on Testing Set |
|---|---|---|---|---|---|
| SiMES | Fundus | 500 | 100% | 5428 | 98.80% |
| SCES | Fundus | 500 | 100% | 1176 | 100% |
| BMES | Fundus | 500 | 100% | 5722 | 99.76% |
| Other Fundus | Fundus | 1200 | 100% | 11114 | 99.26% |
| ACHIKO-NC | Slit-lamp | 500 | 100% | 5030 | 100% |
| AGAR Database | OCT | 500 | 100% | 1164 | 100% |
| AGATE Database | Retcam | 500 | 100% | 3199 | 100% |
| Scenery | Scenery | 2000 | 100% | 2509 | 100% |
| Total | | 6200 | 100% | 35342 | 99.54% |

We now describe the results of the Fundus Image Quality Assessment (step 3). As mentioned above, depending upon the application, the steps 31 and 32 can be performed in the opposite order, and the experimental results below are from an application in which step 32 is performed before step 31.

a) Full Image Assessment (Sub-Step 32)

The algorithm was trained and tested on a database of 740 images, in which 600 images of good quality and 140 images are of poor quality. 123 of the 140 poor quality images are due to existence of cataract, which accounts for about 88%. Others are mainly due to uneven illumination and overexposure during taking. All images are of the dimension of 3072×2048 pixels. In the experiment setting, half of images are used for training (300 good-quality images and 70 poor-quality images) and the other half are used for testing.

Images were classified as high or low quality according to whether the fullRQS for the image was respectively above or below a threshold. The threshold used was set by trial and error. In a commercial application of the embodiment using a given CAD system, the threshold may be set according to the properties of the system as each system can process images with different quality standards.

The algorithm can achieve an accuracy of 94.3% and 91.6% of classification for the training set and testing set respectively. In terms of full image quality score (full RQS), the area under curve (AUC) of the receiver operating characteristic curve achieves 0.967 and 0.958 respectively.

Figure 15:
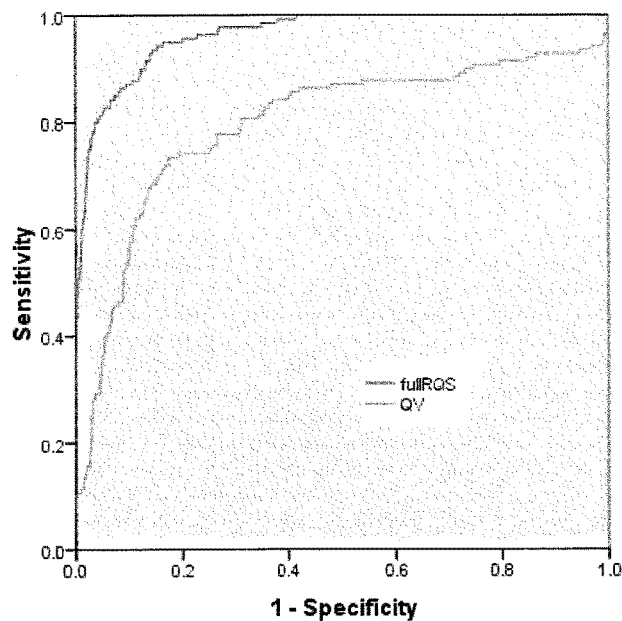
FIG. 15 shows the ROC curve for a full image using an embodiment of the present invention and a prior art system.

For comparison purpose, we implemented a no-reference quality metric ($Q_V$) based on blood vessel trees in the fundus image. Tested on the same data set of 740 images, the $Q_V$ metric achieves an AUC of 0.796. The ROC curves from both methods are shown in FIG. 15. The ROC curve of the full RQS is shown dark, and the ROC curve of the $Q_V$ metric is shown light.

b) Optic Disc ROI Assessment (Sub-Step 31 in the Case that the ROI is Based on the Optic Disc)

For optic disc ROI quality assessment, the ROI images are extracted with a dimension of 800×800 pixels using method explained above. The dataset used for this part is optic ROI images from the full image dataset defined above, and images are labelled as high quality by applying respective thresholds to the full image quality score and the optic disc quality score. The logic for this is that a high (low) quality full image typically has a high (low) quality optic disc region. Table III shows the result of 10-fold cross validation for the fundus image quality classification.

TABLE III

Accuracy of fundus image quality classification

| Fold | Training Set | Testing Set |
|---|---|---|
| 1 | 0.962 | 0.959 |
| 2 | 0.968 | 0.959 |
| 3 | 0.957 | 0.943 |
| 4 | 0.962 | 0.943 |
| 5 | 0.957 | 0.954 |
| 6 | 0.962 | 0.957 |
| 7 | 0.949 | 0.959 |
| 8 | 0.962 | 0.949 |
| 9 | 0.962 | 0.951 |
| 10 | 0.954 | 0.959 |
| Average total | 0.960 | 0.954 |

The ARIES system also produces an OD quality score (odRQS) in the range of 0 to 1. A score that is close to 1 represents a high quality image. On the other hand, a score that is close to 0 indicates a very low quality image. Images can be classified as high or low quality according to whether odRQS is respectively above or below a threshold. In a commercial application of the embodiment using a given CAD system, the threshold may be set according to the properties of the system as each system can process images with different quality standards.

Figure 16:
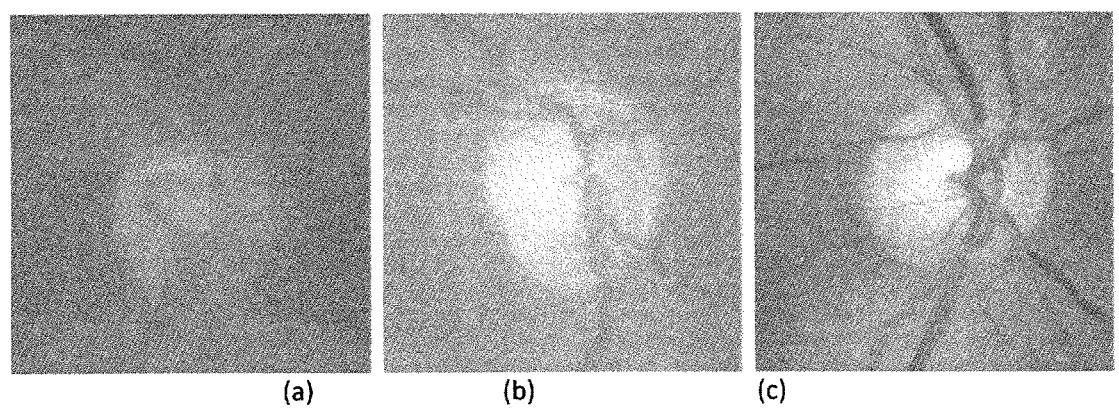
FIG. 16, which is composed of FIGS. 16(a)-(c), shows the optic disc regions of three different fundus images, which are given different quality scores by the method of FIG. 6.

FIG. 16 shows images with different levels of image quality score. FIG. 16(a) has a quality score of 0.30, FIG. 16(b) has a quality score of 0.66, and FIG. 16(c) has a quality score of 0.92.

Figure 17:
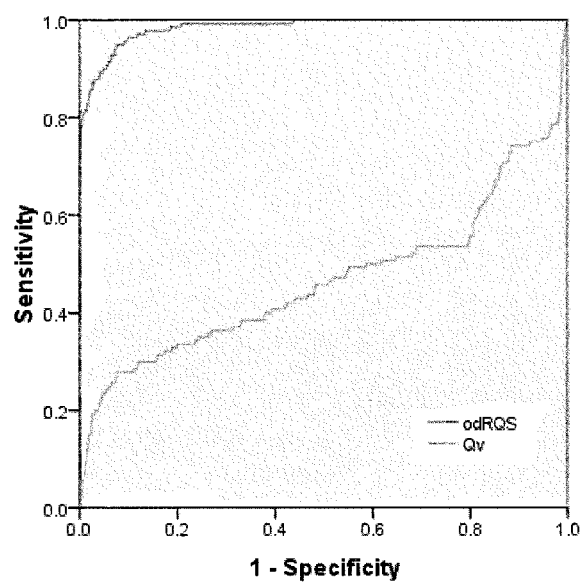
FIG. 17 shows the ROC curve for an optic disk ROI using an embodiment of the present invention and a prior art system.

The $Q_V$ metric is also implemented on the optic disc ROI images, which achieves an AUC of 0.532. However, the proposed optic disc ROI RQS can do a much better job by achieving 0.987 of AUC. The ROC curves are shown in FIG. 17, where the optic disc RQS is shown by the dark line, and the $Q_V$ metric is shown by the light line.

c) Macula ROI Assessment (Sub-Step 31 in the Case that the ROI is Based on the Macula)

The last experiment was performed on macula ROI to test whether an image is good enough to diagnose AMD. Similar to full image and optic disc ROI, the system generates a macula ROI quality score (maculaRQS). This module is trained and tested on a database of 472 images, in which 350 are with good quality macula ROI and 122 are with poor quality macula ROI. The macula detection is achieved using an automatic method. Then, macula ROI is extracted as a 1220×1220 image centred at the macula.

Using half of the dataset for training and the other half for testing, the average classification accuracy can achieve 89% and 86% percent for training and testing datasets in a 10-folder cross validation. Images can be classified as high or low quality according to whether maculaRQS is respectively above or below a threshold. In a commercial application of the embodiment using a given CAD system, the threshold may be set according to the properties of the system as each system can process images with different quality standards.

Figure 18:
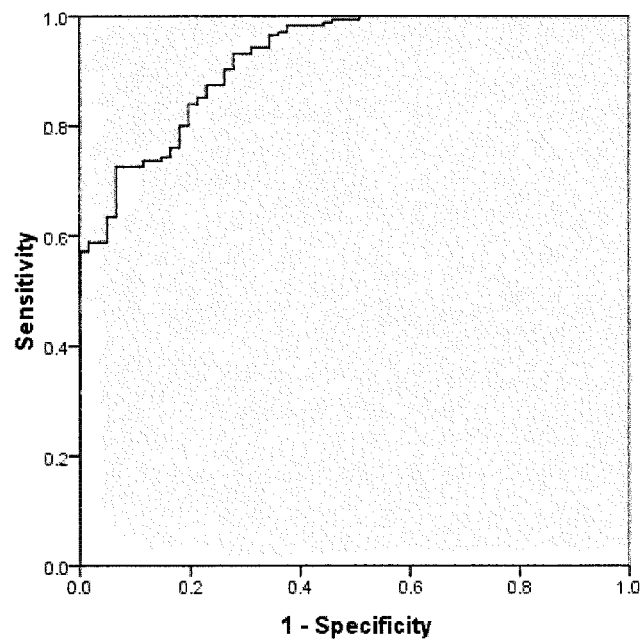
FIG. 18 shows the ROC curve for a macula ROI obtained using an embodiment of the present invention.

The AUC for the maculaRQS metric can be as high as 0.92 for the testing set as shown in FIG. 18, which shows the ROC curve of macula RQS.

Note that each of fullRQS, odRQS and maculaRQS provides an independent means of classifying images as high or low quality. odRQS and maculaRQS are targeted at specific respective ROIs. An image with a high fullRQS score may correspond to a poor quality macula region and high quality OD region, or a high quality macula region and poor quality OD region, or some other combination. Thus, according to the application of the embodiment, and in particular which region(s) of an image which is classified as high quality will be employed in the CAD, a different selection of the RQS values may be selected for use in the classification.

What is claimed is:

1. A computer-implemented method of assessing the quality of at least one retinal image of an eye of a subject, the method including:
    (a) generating at least one quality score for the retinal image by:
        (i) identifying at least one region of interest (ROI) in the retinal image, the ROI being a region image of a predefined structural portion of the eye;
        (ii) extracting one or more region image features of the ROI;
        (iii) generating a region quality score for the ROI, using the region image features extracted for the ROI and an adaptive model;
    (b) generating a full quality score for the full retinal image by:
        (i) extracting one or more full image features of the full retinal image; and
        (ii) generating the full image quality score for the full retinal image, using the full image features extracted for the full retinal image and the adaptive model; and
    (c) assessing the quality of the retinal image by comparing the region quality score and full quality score against predefined criteria,
    wherein the adaptive model is obtained using previously obtained region image features and full image features of retinal images of other eyes.

2. A method according to claim 1 in which there is a ROI for at least one of (i) the optic disk of the eye, and (ii) the macula.

3. A method according to claim 1, wherein the ROI is identified according to a predetermined order of ROIs in the retinal image.

4. A method according to claim 1 in which the extracted features include one or more of:
    a contrast measure;
    a blur measure;
    an entropy measure; and
    a blood vessel density measure.

5. A method of assessing an image comprising:
    determining whether the image is a retinal image;
    if the determination is positive, assessing the quality of the image by a computer-implemented method of assessing the quality of at least one retinal image of an eye of a subject, the method including:
    (a) generating at least one quality score for the retinal image by:
        (i) identifying at least one region of interest (ROI) in the retinal image, the ROI being a region image of a predefined structural portion of the eye;
        (ii) extracting one or more region image features of the ROI;
        (iii) generating a region quality score for the ROI, using the region image features extracted for the ROI and an adaptive model;
    (b) generating a full quality score for the full retinal image by:
        (i) extracting one or more full image features of the full retinal image; and (ii) generating the full image quality score for the full retinal image, using the full image features extracted for the full retinal image and the adaptive model; and (c) assessing the quality of the retinal image by comparing the region quality score and full quality score against predefined criteria, wherein the adaptive model is obtained using previously obtained region image features and full image features of retinal images of other eyes.

6. A method according to claim 5 in which the determination is performed using at least one of:

a process of extracting bag-of-words (BoW) features of the image, and classifying the image using a bag-of-words classifier; and a structural similarity index (SSIM) classification performed by obtaining a numerical measure of the similarity of a plurality of characteristic numerical values of the image and characteristic numerical values of previously-obtained images of other eyes.

7. A method according to claim 6 in which the determination is performed by:

making an initial classification using said bag-of-word classifier; and using said SSIM classification to re-evaluate images which were classified as not being retinal images by the bag-of-word classifier.

8. A method of obtaining information about an eye using a retinal image of the eye, comprising:

assessing the quality of the image by a method including:
(a) generating at least one quality score for the retinal image by:
(i) identifying at least one region of interest (ROI) in the retinal image, the ROI being a region image of a predefined structural portion of the eye;
(ii) extracting one or more region image features of the ROI,
(iii) generating a region quality score for the ROI, using the region image features extracted for the ROI and an adaptive model;
(b) generating a full quality score for the full retinal image by:
(i) extracting one or more full image features of the full retinal image; and
(ii) generating the full image quality score for the full retinal image, using the full image features extracted for the full retinal image and the adaptive model; and
(c) assessing the quality of the retinal image by comparing the region quality score and full quality score against predefined criteria,
wherein the adaptive model is obtained using previously obtained region image features and full image features of retinal images of other eyes;
determining if the quality score(s) meet the predefined criteria; and
if the determination is positive, obtaining the information about the eye by analysing the image.

9. A method of treating an eye comprising:

obtaining information about an eye using a method of assessing an image comprising:
determining whether the image is a retinal image;
if the determination is positive, assessing the quality of the image by a computer-implemented method of assessing the quality of at least one retinal image of an eye of a subject, the method including:
(a) generating at least one quality score for the retinal image by:
(i) identifying at least one region of interest (ROI) in the retinal image, the ROI being a region image of a predefined structural portion of the eye;
(ii) extracting one or more region image features of the ROI;
(iii) generating a region quality score for the ROI, using the region image features extracted for the ROI and an adaptive model;
(b) generating a full quality score for the full retinal image by:
(i) extracting one or more full image features of the full retinal image; and
(ii) generating the full image quality score for the full retinal image, using the full image features extracted for the full retinal image and the adaptive model; and
(c) assessing the quality of the retinal image by comparing the region quality score and full quality score against predefined criteria,
wherein the adaptive model is obtained using previously obtained region image features and full image features of retinal images of other eyes;
wherein the determination is performed using at least one of:
a process of extracting bag-of-words (BoW) features of the image, and classifying the image using a bag-of-words classifier; and
a structural similarity index (SSIM) classification performed by obtaining a numerical measure of the similarity of a plurality of characteristic numerical values of the image and characteristic numerical values of previously-obtained images of other eyes;
wherein the determination is performed by:
making an initial classification using said bag-of-word classifier; and
using said SSIM classification to re-evaluate images which were classified as not being retinal images by the bag-of-word classifier;
performing a diagnostic step using the information;
according to the diagnostic step, selecting a treatment procedure; and
performing the treatment procedure.

10. A computer system comprising a processor and a data storage device storing computer program instructions operative, upon performance of the instructions by the processor, to cause the processor to perform a computer-implemented method of assessing the quality of at least one retinal image of an eye of a subject, the method including:
(a) generating at least one quality score for the retinal image by:
(i) identifying at least one region of interest (ROI) in the retinal image, the ROI being a region image of a predefined structural portion of the eye;
(ii) extracting one or more region image features of the ROI;
(iii) generating a region quality score for the ROI, using the region image features extracted for the ROI and an adaptive model;
(b) generating a full quality score for the full retinal image by:
(i) extracting one or more full image features of the full retinal image; and
(ii) generating the full image quality score for the full retinal image, using the full image features extracted for the full retinal image and the adaptive model; and (c) assessing the quality of the retinal image by comparing the region quality score and full quality score against predefined criteria,
wherein the adaptive model is obtained using previously obtained region image features and full image features of retinal images of other eyes.

11. A non-transitory computer program product, storing computer program instructions operative, upon performance of the instructions by a processor, to cause the processor to perform a computer-implemented method of assessing the quality of at least one retinal image of an eye of a subject, the method including:
  (a) generating at least one quality score for the retinal image by:
    (i) identifying at least one region of interest (ROI) in the retinal image, the ROI being a region image of a predefined structural portion of the eye;
    (ii) extracting one or more region image features of the ROI;
    (iii) generating a region quality score for the ROI, using the region image features extracted for the ROI and an adaptive model;
  (b) generating a full quality score for the full retinal image by:
    (i) extracting one or more full image features of the full retinal image; and
    (ii) generating the full image quality score for the full retinal image, using the full image features extracted for the full retinal image and the adaptive model; and
  (c) assessing the quality of the retinal image by comparing the region quality score and full quality score against predefined criteria,
wherein the adaptive model is obtained using previously obtained region image features and full image features of retinal images of other eyes.

12. A method according to claim 1 wherein the predefined criteria comprise predefined thresholds of the region quality score and full quality score.

13. A method according to claim 1 wherein the region image features and full image features are based on common image quality measures.

14. A method according to claim 8 wherein the region image features and full image features are based on common image quality measures.

* * * * *